(12) United States Patent
Barbera-Guillem

(10) Patent No.: US 6,761,877 B2
(45) Date of Patent: Jul. 13, 2004

(54) FUNCTIONALIZED ENCAPSULATED FLUORESCENT NANOCRYSTALS

(75) Inventor: Emilio Barbera-Guillem, Powell, OH (US)

(73) Assignee: BioCrystal, Ltd., Westerville, OH (US)

( * ) Notice: Subject to any disclaimer, the term of this patent is extended or adjusted under 35 U.S.C. 154(b) by 123 days.

(21) Appl. No.: 09/783,469

(22) Filed: Feb. 12, 2001

(65) Prior Publication Data

US 2002/0001716 A1 Jan. 3, 2002

Related U.S. Application Data

(60) Provisional application No. 60/183,608, filed on Feb. 18, 2000, and provisional application No. 60/183,607, filed on Feb. 18, 2000.

(51) Int. Cl.[7] .............................. A61B 10/00; B32B 9/04
(52) U.S. Cl. ................... 424/9.6; 428/402.24; 428/403; 428/404; 427/213.3; 427/215; 427/220; 424/9.1; 424/9.32; 424/9.321; 424/9.36
(58) Field of Search .......................... 428/402.24, 403, 428/404; 427/213.3, 215, 220; 424/9.1, 9.32, 9.321, 9.34, 9.36, 9.6

(56) References Cited

U.S. PATENT DOCUMENTS

| | | | |
|---|---|---|---|
| 5,525,377 A | 6/1996 | Gallagher et al. | |
| 5,990,479 A | 11/1999 | Weiss et al. | |
| 6,114,038 A | 9/2000 | Castro et al. | |

FOREIGN PATENT DOCUMENTS

| | | |
|---|---|---|
| WO | WO 00/28089 | 5/2000 |

OTHER PUBLICATIONS

Bruchez et al., "Semiconductor nanocrystals as fluorescent biological labels", Science, Sep. 25, 1998, vol. 281, pp. 2013–2015.

Chan and Nie, "Quantum dot bioconjugates for ultrasensitive nonisotopic detection", Science, Sep. 25, 1998, vol. 281, pp. 2016–2018.

Kennedy et al., "Cryo–transmission electron microscopy confirm controlled synthesis of cadmium sulfide nanocrystal within lecithin vesicles", Chem. Mater., 1998, vol. 10 pp. 2116–2119.

Korgel and Monbouquette; "Synthesis of size–monodisperse CdS nanocrystals using phosphatidylcholine vesicles as true reaction components", J. Phys. Chem., 1996, vol. 100, pp. 346–351.

*Primary Examiner*—Samuel A. Acquah
(74) *Attorney, Agent, or Firm*—Raymond A. Miller; Pepper Hamilton LLP

(57) ABSTRACT

Provided are a functionalized, encapsulated fluorescent nanocrystal comprising a liposome having encapsulated therein one or more fluorescent nanocrystals; use of the functionalized, encapsulated fluorescent nanocrystals in detection systems; and a method of producing functionalized, encapsulated fluorescent nanocrystals. A method of using the functionalized encapsulated fluorescent nanocrystals having affinity molecule bound thereto comprises contacting the functionalized encapsulated fluorescent nanocrystals with a sample so that complexes are formed between the functionalized encapsulated fluorescent nanocrystals and substrate for which the affinity molecule has binding specificity, if the substrate is present; exposing the complexes in the detection system to an excitation light source, and detecting a fluorescence peak emitted from the complexes, if present.

8 Claims, No Drawings

FUNCTIONALIZED ENCAPSULATED FLUORESCENT NANOCRYSTALS

This is a nonprovisional application based on copending provisional Application Nos. 60/183607 and 60/183608, both filed Feb. 18, 2000, the disclosures of which are herein incorporated by reference.

FIELD OF INVENTION

This invention relates generally to novel compositions comprising encapsulated, fluorescent nanocrystals. More particularly, the present invention relates to the use of a vesicle or capsid to encapsulate fluorescent nanocrystals in forming water-soluble fluorescent nanocrystals.

BACKGROUND OF THE INVENTION

Nonisotopic detection systems have become a preferred mode in scientific research and clinical diagnostics for the detection of biomolecules using various assays including, but not limited to, flow cytometry, nucleic acid hybridization, DNA sequencing, nucleic acid amplification, microarrays, immunoassays, histochemistry, and functional assays involving living cells. In particular, while fluorescent organic molecules such as fluorescein and phycoerythrin are used frequently in detection systems, there are disadvantages in using these molecules in combination. For example, each type of fluorescent molecule typically requires excitation with photons of a different wavelength as compared to that required for another type of fluorescent molecule. However, even when a single light source is used to provide a single excitation wavelength (in view of the spectral line width), often there is insufficient spectral spacing between the emission optima of different fluorescent molecules to permit individual and quantitative detection without substantial spectral overlap. Additionally, conventional fluorescent molecules have limited fluorescence intensity. Further, currently available nonisotopic detection systems typically are limited in sensitivity due to the finite number of nonisotopic molecules which can be used to label a biomolecule to be detected.

Doped metal oxide ("dMO") nanocrystals are nanocrystals that can be excited with a single excitation light source resulting in a detectable fluorescence emission of high quantum yield (e.g., a single quantum dot having at a fluorescence intensity that may be a log or more greater than that a molecule of a conventional fluorescent dye) and with a discrete fluorescence peak. Typically, they have a substantially uniform size of less than 200 Angstroms, and preferably have a substantially uniform size in the range of sizes of from about 1 nm to about 5 nm, or less than 1 nm. In that regard, dMO nanocrystals are preferably comprised of metal oxides doped with one or more rare earth elements, wherein the dopant comprising the rare earth element is capable of being excited (e.g., with ultraviolet light) to produce a narrow spectrum of fluorescence emission (typically more narrow than the spectrum of fluorescence emission emitted by a semiconductor nanocrystal). Such dMO nanocrystals are well known in the art. However, a desirable feature of dMO nanocrystals when used for nonisotopic detection applications is that the nanocrystals be made water-soluble. "Water-soluble" is used herein to mean that the nanocrystals are sufficiently soluble or suspendable in an aqueous-based solution including, but not limited to, water, water-based solutions, and buffer solutions, that are used in detection processes, as known by those skilled in the diagnostic art.

Semiconductor nanocrystals are quantum dots that can be excited with a single excitation light source resulting in a detectable fluorescence emission of high quantum yield (e.g., a single quantum dot having at a fluorescence intensity that may be a log or more greater than that a molecule of a conventional fluorescent dye) and with a discrete fluorescence peak. Typically, they have a substantially uniform size of less than 200 Angstroms, and preferably have a substantially uniform size in the range of sizes of from about 1 nm to about 5 nm, or less than 1 nm. In that regard, quantum dots are preferably comprised of a Group II–VI semiconductor material (of which ZnS, and CdSe are illustrative examples), or a Group III–V semiconductor material (of which GaAs is an illustrative example). Such quantum dots are well known in the art. However, a desirable feature of quantum dots when used for nonisotopic detection applications is that the quantum dots be made water-soluble. Current methods of making semiconductor nanocrystals water-soluble is to add to the semiconductor nanocrystal a layer comprising mercaptocarboxylic acid (Chen and Nie, 1998, *Science* 281:2016–2018), or silica (U.S. Pat. No. 5,990,479), or one or more layers of amino acids (U.S. Pat. No. 6,114,038). Depending on which layer composition is used, the treated nanocrystal may have limited stability in an aqueous solution, particularly when exposed to air (oxygen) and/or light. More particularly, oxygen and light can cause the molecules comprising the layer to become oxidized, thereby forming disulfides which destabilize the attachment of the layer molecules to the semiconductor nanocrystals. Thus, oxidation may cause the layer molecules to become detached from the surface of the quantum dots, thereby exposing the surface of the quantum dots which may result in "destabilized quantum dots". Destabilized quantum dots form aggregates when they interact together, and the formation of such aggregates eventually leads to irreversible flocculation of the quantum dots. Additionally, depending on the layer composition, it can cause non-specific binding, particularly to one or more molecules in a sample other than the target molecule, which is not desirable in a detection assay.

Hence, there is a need to provide alternative forms of water-soluble, fluorescent nanocrystals.

SUMMARY OF THE INVENTION

It is a primary object of the present invention to provide fluorescent nanocrystals which are encapsulated by a vesicle or capsid comprising a liposome.

It is another object of the present invention to provide fluorescent nanocrystals which are encapsulated by or trapped within a vesicle or capsid comprising a liposome, and wherein the surface of the liposome is functionalized with surface groups comprising a reactive functionality that may be used to form a bond with one or more molecules of an affinity molecule which has a reactive functionality which is capable of forming a bond with the surface groups of the liposome.

It is another object of the present invention to provide a fluorescent nanocrystal which comprises one or more fluorescent nanocrystals encapsulated by or trapped within a liposome, and wherein the surface of the liposome is functionalized with surface groups comprising one or more reactive functionalities.

It is another object of the present invention to provide a functionalized, encapsulated fluorescent nanocrystal which comprises one or more fluorescent nanocrystals encapsulated by or trapped within a liposome which is functionalized by the addition of one or more affinity molecules.

It is further object of the present invention to provide a functionalized, encapsulated fluorescent nanocrystal which comprises one or more fluorescent nanocrystals encapsulated by or trapped within a liposome, and wherein the liposome portion may be disrupted to release the fluorescent nanocrystals in a method of "quenching" the fluorescence in a reaction.

DETAILED DESCRIPTION OF THE INVENTION

Definitions

By the term "fluorescent nanocrystals" is meant, for purposes of the specification and claims to refer to fluorescent nanocrystals comprised of doped metal oxide nanocrystals, semiconductor nanocrystals, or a combination thereof.

By the terms "doped metal oxide nanocrystals" or "dMO nanocrystals" is meant, for purposes of the specification and claims to refer to nanocrystals comprised of: a metal oxide, and a dopant comprised of one or more rare earth elements. For example, suitable metal oxides include, but are not limited to, yttrium oxide ($Y_2O_3$), zirconium oxide ($ZrO_2$), zinc oxide (ZnO), copper oxide (CuO or $Cu_2O$), gadolinium oxide ($Gd_2O_3$), praseodymium oxide ($Pr_2O_3$), lanthanum oxide ($La_2O_3$), and alloys thereof. The rare earth element comprises an element selected from the Lanthanide series and includes, but is not limited to, europium (Eu), cerium (Ce), neodymium (Nd), samarium (Sm), terbium (Tb), gadolinium (Gd), holmium (Ho), thulium (Tm), an oxide thereof, and a combination thereof. As known to those skilled in the art, depending on the dopant, an energized dMO nanocrystal is capable of emitting light of a particular color. Thus, the nature of the rare earth or rare earths are selected in consequence to the color sought to be imparted (emitted) by a functionalized, encapsulated dMO nanocrystal according to the present invention. A given rare earth or rare earth combination has a given color, thereby permitting the provision of functionalized, encapsulated dMO nanocrystals, each of which may emit (with a narrow emission peak) a color over an entire range of colors by adjusting the nature of the dopant, the concentration of the dopant, or a combination thereof. For example, the emission color and brightness (e.g., intensity) of a dMO nanocrystal comprising $Y_2O_3$:Eu may depend on the concentration of Eu; e.g., emission color may shift from yellow to red with increasing Eu concentration. For purposes of illustration only, representative colors which may be provided are listed in Table 1.

TABLE 1

| Fluorescent Color | Dopant |
| --- | --- |
| Blue | thulium |
| Blue | cerium |
| yellow-green | terbium |
| Green | holmium |
| Green | erbium |
| Red | europium |
| reddish orange | samarium |
| Orange | neodymium |
| Yellow | dysprosium |
| White | praseodymium |
| orange-yellow | europium + terbium |
| orange-red | europium + samarium |

Methods for making dMO nanocrystals are known to include, but are not limited to a sol-gel process (see, e.g., U.S. Pat. No. 5,637,258), and an organometallic reaction. As will be apparent to one skilled in the art, the dopant (e.g., one or more rare earth elements) are incorporated into the dMO nanocrystal in a sufficient amount to permit the dMO nanocrystal to be put to practical use in fluorescence detection as described herein in more detail. An insufficient amount comprises either too little dopant which would fail to emit sufficient detectable fluorescence, or too much dopant which would cause reduced fluorescence due to concentration quenching. In a preferred embodiment, the amount of dopant in a dMO nanocrystal is a molar amount in the dMO nanocrystal selected in the range of from about 0.1% to about 25%.

By the term "semiconductor nanocrystals" is meant, for purposes of the specification and claims to refer to quantum dots (crystalline semiconductors) comprised of a core comprised of at least one of a Group II–VI semiconductor material (of which ZnS, and CdSe are illustrative examples), or a Group III–V semiconductor material (of which GaAs is an illustrative example), a Group IV semiconductor material, or a combination thereof. In a preferred embodiment, the core of the quantum dots may be passivated with an semiconductor overlayering ("shell") uniformly deposited thereon. For example, a Group II–VI semiconductor core may be passivated with a Group II–VI semiconductor shell (e.g., a ZnS or CdSe core may be passivated with a shell comprised of YZ wherein Y is Cd or Zn, and Z is S, or Se). As known to those skilled in the art, the size of the semiconductor core correlates with the spectral range of emission, as illustrated in Table 1 for CdSe.

TABLE 1

| Color | Size Range (nm) | Peak Emission Range |
| --- | --- | --- |
| blue | 2.5 to 2.68 | 476 to 486 |
| green | 2.8 to 3.4 | 500 to 530 |
| yellow | 3.58 to 4.26 | 536 to 564 |
| orange | 4.9 to 6.1 | 590 to 620 |
| red | 8.6 to 10.2 | 644 to 654 |

Methods for making semiconductor nanocrystals are known in the art. A preferred method of making semiconductor nanocrystals is by a continuous flow process (U.S. Pat. No. 6,179,912, the disclosure of which is herein incorporated by reference).

By the term "affinity molecule" is meant, for purposes of the specification and claims, to mean a molecule which is capable of binding to another molecule; and in a preferred embodiment, has binding specificity and avidity for a target molecule. In general, affinity molecules are known to those skilled in the art to include, but are not limited to, lectins or fragments (or derivatives) thereof which retain binding function; monoclonal antibodies ("mAb", including chimeric or genetically modified monoclonal antibodies (e.g., "humanized")); peptides; aptamers; nucleobases (synthetic, natural, or modified); nucleic acid molecules (including, but not limited to, single stranded RNA or single-stranded DNA, or single-stranded nucleic acid hybrids); avidin, or streptavidin, or avidin derivatives; and the like. The invention may be practiced using a preferred affinity molecule to the exclusion of affinity molecules other than the preferred affinity molecule. The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include $F(ab')_2$, Fab', Fab, Fv, scFV, Fd' and Fd fragments. Methods for producing the various fragments or derivatives from mAbs are well known in the art. The construction of chimeric antibodies is now a straightforward procedure in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art. Aptamers can be made using methods described in U.S. Pat. No. 5,789,157 (herein incorporated by reference). Lectins, and fragments thereof, are commercially available. Lectins are known to those skilled in the art, and are commercially available.

By the term "nucleobase" is meant, for purposes of the specification and claims to refer to a nucleic acid moiety including, but not limited to: nucleosides (including derivatives, or functional equivalents thereof, and synthetic or modified nucleosides, and particularly, a nucleoside comprising a reactive functionality (e.g., free amino group or carboxyl group); nucleotides (including dNTPs, ddNTPs, derivatives or functional equivalents thereof, and particularly, a nucleotide comprising a reactive functionality (e.g., free amino group or carboxyl group); acyclonucleoside triphosphates (see, e.g., U.S. Pat. No. 5,558,991); 3' (2')-amino-modified nucleosides, 3' (2')-amino-modified nucleotides, 3' (2')-thiol-modified nucleosides, 3' (2')-thiol-modified nucleotides (see, e.g., U.S. Pat. No. 5,679,785); alkynylamino-nucleotides (see, e.g., as a chain terminator, U.S. Pat. No. 5,151,507); and nucleoside thiotriphosphates (see, e.g., U.S. Pat. No. 5,187,085).

By the term "reactive functionality" is meant, for purposes of the specification and claims, to refer to a free chemical group which can bond or associate with a chemical-reactive group (reactive with the free chemical groups). In a preferred embodiment, the resultant bond or association is of sufficient stability to withstand conditions encountered in a method of detection, as known in the art. Free chemical groups include, but are not limited to a thiol, carboxyl, hydroxyl, amino, amine, sulfo, phosphate, or the like; whereas chemical-reactive groups include, but are not limited to, thiol-reactive group, carboxyl-reactive group, hydroxyl-reactive group, amino-reactive group, amine-reactive group, sulfo-reactive group, or the like.

By the term "liposome" is meant, for purposes of the specification and claims, to refer to a generally spherical vesicle or capsid generally comprised of amphipathic molecules (e.g., having both a hydrophobic (nonpolar) portion and a hydrophilic (polar) portion). Typically, the liposome can be produced as a single (unilamellar) closed bilayer or a multicompartment (multilamellar) closed bilayer. The liposome can be formed by natural lipids, synthetic lipids, or a combination thereof. In a preferred embodiment, the liposome comprises one or more phospholipids. In a more preferred embodiment, the liposome is substituted with one or more conventional additives ("a component for substitution"), wherein the one or more additives are selected from the group consisting of a membrane stabilizer, an isotonic agent (e.g., sugars, sodium chloride, polyalcohols such as mannitol, sorbitol, and the like), a pH adjusting agent (e.g., a base, a basic amino acid, an acidic amino acid, sodium phosphate, sodium carbonate, and the like, present in an amount to adjust the liposome to a desired pH), an aggregation minimizer (e.g., a surfactant (e.g., polysorbates, poloxamers), polysaccharide, liposomal surface carboxyl groups, and the like), an affinity molecule, an amino acid, and a combination thereof. As apparent to one skilled in the art, and depending on the lipid composition and the composition of the component for substitution, the one or more components for substitution may be added during the formation of the liposome, may be added after the formation of the liposome, or a combination thereof. A preferred component for substitution of the liposome may be used to the exclusion of components other than the preferred component. For example, a membrane stabilizer is added in an effective amount to increase the stability of a liposome. Stability refers to one or more of membrane integrity, ability to withstand heat (e.g., a temperature above room temperature, and preferably a temperature in the range of from about 35° C. to about 100° C.), ability to withstand oxygen (e.g., as exposed during normal use conditions), ability to withstand light (e.g., as exposed during normal use conditions), and a combination thereof. A membrane stabilizer may comprise one or more sterols (e.g., cholesterol), one or more fatty acids, one or more amino acids, and a combination thereof. Also, stability, with respect to exposure to oxidation, may be enhanced by nitrogen gas substitution using methods known on the art. Lipids known in the art for forming liposomes include, but are not limited to, lecithin (soy or egg; phosphatidylcholine), dipalmitoylphosphatidylcholine, dimyristoylphosphatidylcholine, distearoylphosphatidylcholine, dicetylphosphate, phosphatidylglycerol, hydrogenated phosphatidylcholine, phosphatidic acid, cholesterol, phosphatidylinositol, a glycolipid, phosphatidylethanolamine, phosphatidylserine, a maleimidyl-derivatized phospholipid (e.g., N-[4(p-maleimidophenyl)butyryl] phosphatidylethanolamine), dioleylphosphatidylcholine, dipalmitoylphosphatidylglycerol, dimyristoylphosphatidic acid, and a combination thereof. It will be apparent to one skilled in the art that the ratio of the one or more lipids and the one or more components for substitution will depend on factors including, but not limited to, the composition of the lipids, the intended function of each lipid (e.g., the reason for its inclusion in the liposome), the composition of the component for substitution, the intended function of each component for substitution (e.g., the reason for its inclusion in the liposome), and the desired properties of the liposome portion of a functionalized, encapsulated fluorescent nanocrystal (e.g., size of interior space or "capture volume", pH range of stability, temperature range of stability, desired surface charge, desired surface free chemical group). In that regard, as known to those skilled in the art, a particular lipid or lipid combination, when used to form a liposome, can offer particular benefits. For example, inclusion of phosphatidylglycerol in combination with other lipids (e.g., with phosphatidylcholine and cholesterol, ratio of 1:9:8) imparts a negative charge to the liposome which increases intralamellar spacing (capture volume), reduces aggregation, and facilitates initial hydration of the lipid. In a preferred embodiment, the liposomes encapsulating the fluorescent nanocrystals are stable at a neutral pH of from about 6 to about 7; and in a more preferred embodiment, are stable in a broad pH range of from about 4 to about 12. A preferred liposome (content and composition) may be formed as part of the functionalized, encapsulated fluorescent nanocrystals according to the present invention to the exclusion of liposomes other than the preferred liposome.

By the term "functionalized, encapsulated fluorescent nanocrystal" is meant, for purposes of the specification and claims to refer to one or more fluorescent nanocrystals which have been encapsulated (e.g., without establishing a chemical linkage or bond between the one or more fluorescent nanocrystals and the liposome) by a liposome; wherein the outer surface of the liposome is functionalized with surface groups comprising one or more reactive functionalities, one or more affinity molecules, or a combination thereof; and wherein the functionalized, encapsulated fluorescent nanocrystal is water-soluble. In one preferred embodiment, a single fluorescent nanocrystal is encapsulated by the liposome. In another preferred embodiment, a plurality of fluorescent nanocrystals are encapsulated by a liposome. It will be apparent to one skilled in the art that the number of fluorescent nanocrystals encapsulated per liposome can be controlled by factors that include, but are not limited to, the size of the liposome formed, the method in which the fluorescent nanocrystals are encapsulated, post production processing by size exclusion, and the ratio of fluorescent nanocrystals to lipid mixture during formation. It will also be apparent to one skilled in the art, that where a plurality of fluorescent nanocrystals are encapsulated by a liposome, the fluorescent nanocrystals may be homogeneous (i.e., capable of fluorescing essentially the same color) or may be heterogenous (e.g., comprising different populations wherein each population is capable of fluorescing a different (spectrally distinguishable) color than another population of fluorescent nanocrystal that is encapsulated).

By the term "strand synthesis" is meant for purposes of the specification and claims to refer to the production of one more strands, or portions thereof, such as through enzymatic copying by an enzyme which replicates nucleic acids in a template-directed manner. There is no particular size, length or content limitations for the strand. Thus, "strand synthesis" encompasses processes including, but not limited to, nucleic acid amplification, DNA sequencing, fill-in reactions, reverse transcription, in vitro mutagenesis, cycled chain termination sequence reactions, cycled primer extension reactions, random primer extension reactions, nick translations, primer elongation, methods for determining the presence and quantifying the number of di- and trinucleotide repeats (see, e.g., U.S. Pat. No. 5,650,277), and DNA typing with short tandem repeat polymorphisms (see, e.g., U.S. Pat. No. 5,364,759). The nucleic acid composition of the strand synthesized may be selected from molecules which include nucleobases; and more preferably, ribonucleotides (RNA), or deoxyribonucleotides (DNA).

DETAILED DESCRIPTION OF THE INVENTION

This invention relates to compositions comprising functionalized, encapsulated fluorescent nanocrystals. Preferably, the functionalized, encapsulated fluorescent nanocrystals are water-soluble, and can be stored without significant leakage (of the one or more fluorescent nanocrystals from the liposome) over long periods of time. The outer surface of the liposome portion (e.g., polar head groups in contact with the surrounding aqueous environment) is functionalized with surface groups comprising one or more reactive functionalities, one or more affinity molecules, or a combination thereof. As known to those skilled in the art, dMO nanocrystals and semiconductor nanocrystals are generally soluble in organic solvents, and have limited or no solubility in aqueous environments. Thus, a method for removing fluorescence from the aqueous environment containing functionalized, encapsulated fluorescent nanocrystals comprises contacting the functionalized, encapsulated fluorescent nanocrystals with an effective amount of a disrupting agent ("lipolytic agent") to disrupt the liposome portion of the functionalized, encapsulated fluorescent nanocrystals thereby releasing the fluorescent nanocrystals into the aqueous environment with resultant precipitation out of solution.

As general guidance for producing functionalized, encapsulated fluorescent nanocrystals according to the present invention, there are various methods for forming liposomes which may be suitable for encapsulating fluorescent nanocrystals. In one embodiment, the lipids (e.g., phospholipids and sterol) for forming the liposomes, and the fluorescent nanocrystals to be encapsulated, are dissolved in a suitable solvent (e.g., chloroform), and the solvent is evaporated in vacuo to result in a film comprising the lipids and fluorescent nanocrystals ("dried lipid mixture film"). For example, the lipids, fluorescent nanocrystals, and the organic solvent may be added to and mixed in a rotoevaporator flask, and dried under vacuum in a rotary evaporator until the contents form a thin homogenous film. Alternatively, a dried lipid mixture film may be formed by forming a dried lipid film, and adding to that dried lipid film a dried preparation of fluorescent nanocrystals. An aqueous solution is then added to the dried lipid mixture film, and the film is allowed to hydrate (e.g., for between 10–30 minutes at room temperature) resulting in spontaneous formation of liposomes which encapsulate fluorescent nanocrystals. The lipid dispersion may then be vigorously vortexed (e.g., 45 to 60 minutes) to facilitate continued formation of functionalized, encapsulated fluorescent nanocrystals. If desired, the lipid bilayers may be annealed by heating the dispersion to about 45 to 50° C. followed by a gradual cooling to about 4° C. It will be apparent to one skilled in the art that one or more components for substitution of the liposome may be suspended in the aqueous solution prior to the addition of the aqueous solution to the dried lipid mixture film. Alternatively, the liposome portion of the functionalized, encapsulated fluorescent nanocrystals may be post-treated (treated subsequent to formation) with one or more components for substitution of the liposome portion. For example, an aqueous solution containing the one or more components for substitution may be in prolonged contact (e.g., incubated overnight) with the functionalized, encapsulated fluorescent nanocrystals. As another alternative embodiment, the aqueous solution containing the one or more components for substitution, and dried lipid mixture film may be mixed together and strongly vortexed, followed by extrusion of the mixture under pressure through a membrane filter (e.g., polycarbonate) of a desired pore size to obtain a solution containing functionalized, encapsulated fluorescent nanocrystals. In another alternative embodiment, the one or more components for substitution are suspended in an aqueous solution, and then lyophilized. The lyophilized residue is then dissolved in a glycerol buffer (e.g., a 2% glycerol solution containing 0.5 mM EDTA, pH 6.0), and filtered through a membrane filter (e.g., polycarbonate) of a desired pore size. The resultant filtrate is added to the dried lipid mixture film, and the resultant mixture is then hydrated with an aqueous solution and vortexed to form functionalized, encapsulated fluorescent nanocrystals. If desired, the formed functionalized, encapsulated fluorescent nanocrystals may then be extruded through a membrane filter (e.g., polycarbonate) of a desired pore size. In any of these embodiments, the functionalized, encapsulated fluorescent nanocrystals would remain soluble in the aqueous solution in which they are formed, whereas unencapsulated fluorescent nanocrystals may eventually precipitate; hence, a purification may be achieved between functionalized, encapsulated fluorescent nanocrystals and unencapsulated fluorescent nanocrystals.

As will be apparent to one skilled in the art, there are various known methods for producing liposomes that may also be useful for producing functionalized, encapsulated fluorescent nanocrystals. Such methods may include, but are not limited to, a vortexing method, an ultrasonic method, an extrusion method, a reverse-phase evaporation method, a solvent injection method, a surfactant (e.g., detergent)-removal method, an annealing method, and a forced extrusion following freeze-thaw cycles. Each method may offer an advantage; thus, a combination of methods may be desirable (for a review, see, Szoka and Papahadjopoulos, 1981, Chapter 3 in "Liposomes: From Physical Structure to Therapeutic Applications", the contents of which are herein incorporated by reference). For example, sonication is a method used to produce liposomes of a relatively small size as compared to other methods; however, the size is largely heterogenous. By extrusion through a membrane of a defined size, or series of membranes with pores of decreasing diameter, size heterogeneity can be reduced, thereby resulting in liposomes of a well-defined and narrow size dispersion. In another example, sonication may result in liposomes incorporating structural defects. However, annealing (at a temperature above the $T_c$ of the highest melting lipid in the mixture used to form the liposome; e.g., for 30 minutes) can stabilize liposomes (note though, annealing is generally not effective when the liposome is composed of an equimolar ratio of phospholipid and cholesterol). The above principles can be applied to methods for producing functionalized, encapsulated fluorescent nanocrystals.

The selection and molar ratio of the combination of lipids, with or without one or more components for substitution, for encapsulating fluorescent nanocrystals may depend on factors which include, but are not limited to, the application in which the functionalized, encapsulated fluorescent nanocrystals are to be used, the desired surface groups comprising one or more reactive functionalities, desired size and/or stability and/or surface charge of the functionalized, encapsulated fluorescent nanocrystals, and the one or more methods used to make the functionalized, encapsulated fluorescent nanocrystals. Although various combinations may be used, a preferred combination may be selected from two general groupings of suitable lipid mixtures for forming the functionalized, encapsulated fluorescent nanocrystals according to the present invention: a combination of phospholipids with a sterol, wherein a phospholipid in the greatest amount of the combination (as compared to the amounts of the one or more remaining phospholipids of the combination) is in approximate equimolar ratio with the sterol; and a combination of phospholipids with a sterol, wherein the sterol is not in approximate equimolar ratio with the phospholipid comprising the highest amount (concentration) in the combination (as compared to the amounts of the one or more remaining phospholipids of the combination). Either combination may further comprise one or more components for substitution of the liposome portion of the functionalized, encapsulated fluorescent nanocrystals, as described herein in more detail. For purposes of illustration only, and not limitation, combinations of lipids (including with exemplary molar ratios) that may be useful in making the compositions according to the present invention include, but are not limited to, phosphatidylcholine ("PC")/cholesterol ("ch")/phosphatidylserine ("PS"), 5:4:1; PC/ch/phosphatidylglycerol ("PG"), 8:2:1.2 or 9:8:1 or 9:5:1; PC/ch/phosphatidylethanolamine, 6:2:2 or 5:4:1; and dipalmitoylPC/ch/phosphatidic acid, 7:2:1. In a preferred embodiment, a combination of lipids may further comprise one or more components for substitution which is added to the lipids in parts by weight (as expressed in relation to the lipid mixture wherein the total lipid mixture comprises 1 part by weight) in a range of from about 0.0001 to about 0.5, depending on the nature of the one or more components, and the intended function. A preferred combination of lipids and one or more components for substitution may be used to the exclusion of combinations other than the preferred combination in producing the functionalized, encapsulated fluorescent nanocrystals according to the present invention. Similarly, a preferred fluorescent nanocrystal may be used to the exclusion of a fluorescent nanocrystal other than the preferred fluorescent nanocrystal in producing the functionalized, encapsulated fluorescent nanocrystals according to the present invention.

In another preferred embodiment, the one or more affinity molecules desired to be incorporated as part of a functionalized, encapsulated fluorescent nanocrystals is added in the process of producing functionalized, encapsulated fluorescent nanocrystals. In this preferred embodiment, it is desirable that the affinity molecule be comprised of a hydrophobic portion and a hydrophilic portion so that its hydrophobic portion will facilitate interaction with the hydrophobic portion of the lipids in the lipid mixture in forming the liposome portion of the functionalized, encapsulated fluorescent nanocrystals; and its hydrophilic portion will extend out from the surface of the functionalized, encapsulated fluorescent nanocrystals. For example, a dried lipid mixture comprising dried lipids, a dried preparation of the fluorescent nanocrystals, and a dried (e.g., lyophilized) preparation of the affinity molecule comprising a protein (e.g., monoclonal antibody, or peptide, or glycoprotein, or lipoprotein, etc.) is hydrated by the addition of an aqueous solution (alternatively, the affinity molecule is suspended in the aqueous solution); and the resultant dispersion is then vigorously vortexed to facilitate formation of functionalized, encapsulated fluorescent nanocrystals which have incorporated in the liposome portion the one or more affinity molecules. It will be apparent to one skilled in the art that, as compared to neutral phospholipids (e.g., PC), anionic phospholipids (e.g., PG and PS) enhance the binding of the affinity molecule in the liposome portion of the functionalized, encapsulated fluorescent nanocrystals. It will be apparent to one skilled in the art that the amount of affinity molecule to be incorporated, and the content (ratio) and composition of the lipid mixture will depend on the specific affinity molecule to be incorporated as well as the desired application of use for the functionalized, encapsulated fluorescent nanocrystals. In an illustrative, non-limiting example, the lipid mixture may comprise PC/ch/PG (17:5:2.5) and the affinity molecule comprises a peptide in an amount that is in a range of from about 0.001 mg/ml to about 1 mg/ml. As described in more detail herein, one or more components for substitution may be added. Additionally, if desired, the functionalized, encapsulated fluorescent nanocrystals may be subjected to a purification process such as size exclusion, or separation by function, or other method known in the art for purification.

The following examples are provided to further describe the invention, but are not to be considered limitative of the invention.

EXAMPLE 1

This example is a non-limiting illustration of a method of making the functionalized, encapsulated fluorescent nanocrystals according to the present invention. dMo nanocrystals comprising yttrium oxide doped with europium were encapsulated to form functionalized, encapsulated dMO nanocrystals. Briefly, this was performed as follows. A first solution was comprised of droplets of a solution comprising a metal salt (yttrium salt and europium salt) solubilized in water, a surfactant (non-ionic, cationic or ionic) and an oil (e.g., octane). The surfactant can be a lipid mixture or other suitable bipolar molecule (e.g., cetyltrimethylammonium bromide). The approximate ratio of the metal salt solution-:surfactant:oil was 10:15:85. A second solution was comprised of droplets of a solution comprising a hydroxide (ammonium hydroxide) solubilized in water, a surfactant, and an oil, at an approximate ratio of 10:15:85. The first solution and the second solution were mixed (e.g., stirred), thereby resulting in the formation of fluorescent nanocrystals comprised of yttrium oxide doped with europium, and the encapsulation of the fluorescent nanocrystals. The ratio of metal salt in the first solution to hydroxide in the second solution was approximately 1:2. The mixed solution was the centrifuged to pellet the functionalized, encapsulated fluorescent nanocrystals. The functionalized, encapsulated fluorescent nanocrystals were then washed to remove loose surfactant and oil (followed by pelleting), and then resuspended in water.

If desired, the suspension comprising functionalized, encapsulated fluorescent nanocrystals may be further purified (e.g., separating functionalized, encapsulated fluorescent nanocrystals from liposomes not containing fluorescent nanocrystals) or selected for size using methods known in the art. For example, the suspension may be overlayed onto a density gradient solution (e.g., sucrose, or glycerol, or Ficoll) and then centrifuged for a sufficient time to achieve the desired separation of liposome species that may be present in the suspension. In continuing this example, functionalized, encapsulated fluorescent nanocrystals would have a greater density than liposomes not containing fluorescent nanocrystals. Hence, the density gradient may be exposed to an excitation wavelength spectra, and the fluorescing band comprising functionalized, encapsulated fluorescent nanocrystals may then be harvested from the rest of the density gradient. Alternatively, functionalized, encapsulated fluorescent nanocrystals may be further purified using size exclusion chromatography, or by magnetic separation.

EXAMPLE 2

This example is a non-limiting illustration of a method of making the functionalized, encapsulated fluorescent nanocrystals according to the present invention. Semiconductor nanocrystals comprising CdSe core, ZnS shell, of a size of about 7.6 nm (core size of about 5.1 nm), and having a peak emission spectra of about 606 nm, were prepared for encapsulation. The semiconductor nanocrystals (100 ul of a $7 \times 10^{-6}$ M pyridine solution) were precipitated in a microfuge tube with 500 ul of hexanes. The mixture was centrifuged to pellet the semiconductor nanocrystals, the hexanes/pyridine supernatant was discarded, and the pellet was then resuspended in 100 ul of DMSO (dimethyl sulfoxide). The DMSO solution containing the semiconductor nanocrystals was mixed with 0.9 ml of chloroform. The solution was then extracted twice with 500 ul of water to remove the DMSO. The solution was then centrifuged to remove insoluble material, and the supernatant containing solubilized semiconductor nanocrystals was then decanted, and stored (4° C.) until use. To encapsulate the semiconductor nanocrystals, utilized was a lipid mixture comprising phosphatidylchloline (PC) and cholesterol (ch) at a ratio of 5:2. Into a flask containing 1 ml of chloroform was added 100 $\mu$l of the solution comprising the solubilized semiconductor nanocrystals. With stirring, PC (15 mg) was added to the mixture, and then ch (6 mg) was added to the mixture. A schlenk adapter was attached to the flask and the solvent contained therein was removed under vacuum to produce a dried lipid mixture film with semiconductor nanocrystals. To the film was added 3 ml of distilled water, and the solution was then sonicated in a water bath for 20 minutes. The resultant suspension containing functionalized, encapsulated fluorescent nanocrystals was extruded through a 0.2 um syringe filter. Examination by fluorescence microscopy confirmed formation of functionalized, encapsulated fluorescent nanocrystals of a narrow size distribution.

If desired, the suspension comprising functionalized, encapsulated fluorescent nanocrystals may be further purified (e.g., separating functionalized, encapsulated fluorescent nanocrystals from liposomes not containing fluorescent nanocrystals) or selected for size using methods known in the art, as described in Example 1 herein in more detail. It will be apparent to one skilled in the art from the descriptions herein that a functionalized, encapsulated fluorescent nanocrystal may comprise a combination of one or more dMO nanocrystals and one or more semiconductor nanocrystals (preferably, each population of nanocrystal being spectrally distinguishable from other populations of nanocrystals in the combination of nanocrystals). Thus, for example, an organic solution comprising dMO nanocrystals (e.g., comprising yttrium oxide doped with europium and having a peak emission spectra that is spectrally distinguishable from the CdSe/ZnS nanocrystals having a peak emission spectra of about 606 nm) and semiconductor nanocrystals (e.g., CdSe/ZnS nanocrystals having a peak emission spectra of about 606 nm) may be mixed with the phospholipids as described herein in producing a dried lipid mixture film. The dried lipid film may then be treated, as described in this Example 2, to produce functionalized, encapsulated fluorescent nanocrystals.

EXAMPLE 3

This example illustrates functionalized, encapsulated fluorescent nanocrystals according to the present invention. As described herein in more detail, encapsulated fluorescent nanocrystals may be functionalized by comprising surface groups comprising one or more reactive functionalities which are capable of bonding to a reactive functionality of, and which may be used to bond the liposome portion to, an affinity molecule. Thus, a combination of reactive functionalities may be used to label an affinity molecule with a functionalized, encapsulated fluorescent nanocrystal. If desired, as a separate step in the reaction, free reactive functionalities that may be present after the labeling process may be blocked or deactivated using methods known in the art (e.g., by adding a molecule which binds to the free reactive functionality). After the reaction in which the reactive functionality combination is used to perform the labeling, an affinity molecule labeled with a functionalized, encapsulated fluorescent nanocrystal may be separated from unbound affinity molecule and unbound (not bond to affinity molecule) functionalized, encapsulated fluorescent nanocrystal by one or more methods known in the art including, but not limited to chromatography, and size fractionation. A preferred reactive functionality combination may be used to the exclusion of a reactive functionality combination other than the preferred reactive functionality combination.

3.1 Reactive functionality combination comprising amino groups and amino-reactive groups.

In one preferred embodiment, the functionalized, encapsulated fluorescent nanocrystals comprise surface groups comprising free amino groups provided by a lipid, a component for substitution, or a combination thereof. In one preferred embodiment, the free amino groups are provided by including an aminolipid in the lipid mixture which forms the liposome portion of the functionalized, encapsulated fluorescent nanocrystals. For example, molecules of phosphatidylserine, phosphatidylethanolamine ("PE"), or dioleoyl PE, when incorporated in the liposome portion, provides primary amino groups which are free to react and chemically bond with one or more affinity molecules having one or more amino-reactive groups. In one preferred embodiment, an affinity molecule comprising a nucleobase having a reactive functionality comprising a free amino-reactive group (e.g., a carboxyl group) can be chemically bonded to a surface group comprising a free amino group using methods known in the art. Briefly, the nucleobase is esterified by treatment with EDC (1-ethyl-3-[3-dimethylaminopropyl] carbdiimide) followed by treatment with sulfo-NHS at ambient temperature in buffered aqueous solution (at about pH 7.4; e.g., for 30 minutes). 2-mercaptoethanol is added to the solution (e.g., at a concentration of 20 mM), and the mixture is stirred (e.g., for 15 minutes) to quench any unreacted EDC. The activated nucleobase is then contacted with a mol concentration of the functionalized, encapsulated fluorescent nanocrystals (depending on the size, and desired number) for coupling an appropriate and desired number of nucleobase molecules (e.g., one, or if desired, more than one) to a functionalized, encapsulated fluorescent nanocrystal, and the reaction mixture is stirred (e.g., for 2 hours or reacted in other suitable conditions for forming an amide bond between the EDC-activated carboxylates of the nucleobase molecules and the amine groups of the functionalized, encapsulated fluorescent nanocrystals). Ethanolamine is then added (e.g., at a concentration of 30 mM) to quench the coupling reaction (e.g., with stirring for 30 minutes). The resulting solution is then filtered and/or dialyzed to remove excess reagents. The result is the production of functionalized, encapsulated fluorescent nanocrystals having a nucleobase covalently coupled thereto (e.g., a nucleobase labeled with a functionalized, encapsulated fluorescent nanocrystal).

In another preferred embodiment, covalently coupled to surface groups comprising the free amino groups of functionalized, encapsulated fluorescent nanocrystals are nucleobases having free amino groups, via the usage of a component for substitution comprising a spacer arm which terminates at each end with an amino-reactive group. Spacer arms are known in the art to include a chemical (glutaraldehyde), a hydrocarbon chain, and a peptide. For example, the surface groups comprising the free amino groups may be activated by incubating the functionalized, encapsulated fluorescent nanocrystals with a solution containing glutaraldehyde (e.g., 25%, at 20° C. for 10 minutes), followed by dialysis to remove excess glutaraldehyde. The activated functionalized, encapsulated fluorescent nanocrystals are then contacted with a solution of the nucleobase containing the free amino-reactive groups in a mol concentration for coupling the desired number of nucleobase molecules to a functionalized, encapsulated fluorescent nanocrystal. If desired, any free reactive functionalities may be blocked (e.g., by addition of ethanolamine). The resulting solution is then filtered and/or dialyzed to remove excess reagents. The result is the production of functionalized, encapsulated fluorescent nanocrystals having a nucleobase covalently coupled thereto (e.g., a nucleobase labeled with a functionalized, encapsulated fluorescent nanocrystal).

3.2 Reactive functionality combination comprising thiol groups and thiol-reactive groups.

In another preferred embodiment, the nucleobase is labeled with (bonded or coupled to) a functionalized, encapsulated fluorescent nanocrystal according to the present invention by using reactive functionalities comprising thiol group and thiol-reactive groups.

3.2(a) For example, as previously described herein, the functionalized, encapsulated fluorescent nanocrystals may have surface groups comprising free amino groups. These surface groups may be further functionalized by the addition (either in the presence or absence of EDC) of a maleimide derivative that reacts with amino groups. Such a maleimide derivative may include, but is not limited to 3-maleimidopropionic acid N-hydroxysuccinimide ester, 3-maleimidopropionic acid, 3-maleimidobenzoic acid N-hydroxysuccinimide ester, 4-(maleimido-methyl)-1-cyclo-hexanecarboxylic acid N-hydroxysuccinimide ester. The resultant functionalized, encapsulated fluorescent nanocrystals, having a thiol-reactive group, can interact with and bond to a nucleobase previously derivatized with one or more thiol groups.

3.2 (b) As an alternative, the functionalized, encapsulated fluorescent nanocrystals having surface groups comprising free amino groups and molecules of the nucleobase having thiol groups are mixed together in the presence of a component for substitution comprising a cross-linking reagent. The cross-linking reagent has an amino-reactive group at one end, and a thiol-reactive group at the other end. Such cross-linking reagents are known to those skilled in the art to include, but are not limited to, sulfosuccinimidyl 6-[3'-(2 pyridyldithio)-propionamido]hexonate, N-succini-midyl-[4-vinylsulfonyl]benzoate, sulfosuccinimidyl-[4-iodoacetyl] aminobenzoate, N-succinimidyl-[4-iodoacetyl] aminobenzoate, and N-succinimidyl iodoacetate, succinimidyl 3-[bromoacetamido]propionate.

In either of the embodiments illustrated in 3.2(a) or (b), the functionalized, encapsulated fluorescent nanocrystals having reactive functionalities comprising a thiol-reactive group (e.g., as part of a lipid or as a result of a cross-linking reagent) can be contacted with, in suitable conditions for bonding to, a nucleobase previously derivatized with one or more thiol groups. The suitable conditions depends on factors including whether a cross-linking reagent is used, the nature of the cross-linking reagent, and the desired number of molecules of functionalized, encapsulated fluorescent nanocrystals to be labeled to the affinity molecule. When using a commercial cross-linking reagent, suitable conditions are often specified by the manufacturer. Nucleobases can be derivatized to include thiol groups using methods known to those skilled in the art (see, e.g., U.S. Pat. No. 5,679,785, herein incorporated by reference). For example, the OH group located in the 3' and/or 2' position of a nucleobase may be derivatized to a thiol group, thereby allowing interaction with the thiol-reactive group of a functionalized, encapsulated fluorescent nanocrystal, in forming thioether bonds that couple the nucleobase to the functionalized, encapsulated fluorescent nanocrystal. In another example, the 3'-O-position and/or the 2'-O-position of a nucleobase may be derivatized to include alkylthiol chemical functionality, which then can be treated with acid under conditions which remove the thiol-protecting group (see, e.g., U.S. Pat. No. 5,578,718). Thus, the nucleobase may be derivatized to include a thiol group, thereby allowing interaction with the thiol-reactive group of a functionalized, encapsulated fluorescent nanocrystal, in forming thioether bonds that couple the nucleobase to the functionalized, encapsulated fluorescent nanocrystal (e.g., a nucleobase labeled with a functionalized, encapsulated fluorescent nanocrystal).

3.2(c) As yet another alternative, a relatively small (with respect to mol concentration of one or more other lipids used in the lipid mixture; e.g., 20:10:1; PC/ch/DPET) amount of a thiol group-containing lipid may be present in the lipid mixture in producing the functionalized, encapsulated fluorescent nanocrystals. Such a lipid comprises distearolylphosphatidyl ethanolamidomethyl thioacetate ("DPET"). The surface groups of the lipid portion may be modified with hydroxylamine in deprotecting the thiol groups, thereby resulting in free thiol groups. A cross-linking agent may be used which has a thiol-reactive group at one end and an amino-reactive group at the other end (see, e.g., 3.2 (b) herein). Thus, the functionalized, encapsulated fluorescent nanocrystals having free thiol groups, a cross-linking reagent, and a nucleobase having a free amino group are mixed together under suitable conditions for the nucleobase to be labeled by the functionalized, encapsulated fluorescent nanocrystals. Nucleobases can be derivatized with amino groups using methods known to those skilled in the art. For example, the OH group located in the 3' and/or 2' position of a nucleobase may be derivatized to include an amino group. Alternatively, a proparglyethoxyamino nucleoside may be used as a chain-terminating nucleobase, wherein the reactive functionality of this chain-terminating nucleobase comprises the primary amino moiety or the secondary amino moiety. As will be apparent to one skilled in the art from the descriptions herein, other combinations of reactive functionalities may be used to label an affinity molecule with a functionalized, encapsulated fluorescent nanocrystal. For example, a functionalized, encapsulated fluorescent nanocrystal comprising a thiol group-containing lipid (as described herein in 3.2 (c)) may be coupled to a thiol-derivatized affinity molecule comprising a nucleobase (as described herein in 3.2 (b)) using a cross-linking reagent having a thiol-reactive group at either end (e.g., 1,4-bis-maleimidobutane; 1,4-bis-maleimidyl-2,3-dihydroxybutane).

EXAMPLE 4

This example further illustrates functionalized, encapsulated fluorescent nanocrystals according to the present invention. As described in Example 3 herein in more detail, encapsulated fluorescent nanocrystals may be functionalized by comprising surface groups comprising one or more reactive functionalities which are capable of bonding to a reactive functionality of, and which may be used to bond the liposome portion to, an affinity molecule. Thus, a combination of reactive functionalities may be used to label an affinity molecule with a functionalized, encapsulated fluorescent nanocrystal. In Example 3, an affinity molecule was illustrated as comprising a nucleobase. However, as apparent to one skilled in the art from the descriptions herein, other types of affinity molecules can similarly be coupled to functionalized, encapsulated fluorescent nanocrystals according to the present invention.

For example, and with the teachings of Example 3 in mind, the affinity molecule may comprise a protein (e.g., a glycoprotein, peptide, lipoprotein, monoclonal antibody, an antibody fragment with binding specificity, a lectin, avidin, and the like) having a reactive functionality comprising an amine group which can be used to couple to the reactive functionality of functionalized, encapsulated fluorescent nanocrystals using methods known in the art. Alternatively, the protein may comprise a reactive functionality comprising one or more free thiol groups. To continue with this illustration, sulfhydryl (thiol) groups of an antibody may be produced by reduction with a thiol reagent. For example, the antibody (e.g., 20 mg/ml in buffer, pH 8.7) may be treated with 2-mercaptoethanol (e.g., final concentration of 25 mM) under suitable conditions (e.g., 4° C. for 10 minutes) to reduce the protein to contain free thiol groups. The treated antibody may be purified (e.g., by size exclusion), and the number of sulfhydryl groups per mole of antibody can be determined (e.g., Ellman reaction); and thus, preferably an antibody having 2 to 3 free thiol groups is then reacted in a coupling reaction with the functionalized, encapsulated fluorescent nanocrystals (e.g., with or without a coupling reagent, depending on the reactive functionalities and the coupling reaction used). Other reducing agents, such as dithiothreitol, may be used to reduce a disulfide group of an antibody or Fab fragment to a reactive functionality comprising a free sulfhydryl group. As yet another alternative, the protein may comprise a reactive functionality comprising one or more free carboxyl groups. In one illustration, and using methodology described in more detail in Example 3 herein, a free carboxyl group of the protein may be esterified which then allows coupling, in a coupling reaction, with a free amino group of the functionalized, encapsulated fluorescent nanocrystals.

In another preferred embodiment, the affinity molecule which is labeled with functionalized, encapsulated fluorescent nanocrystals comprises a nucleic acid molecule (e.g., oligonucleotide, primer, probe, aptamer, vector, molecular probe, and the like). For example, by adjusting factors which include, but are not limited to, the number of free reactive functionalities per molecule, the ratio and/or number of different molecules to be coupled per coupling reaction, and a combination thereof, a functionalized, encapsulated fluorescent nanocrystal may be produced which is selected from the group consisting of a nucleic acid molecule labeled with a plurality of functionalized, encapsulated fluorescent nanocrystals, a nucleic acid molecule labeled with a single functionalized, encapsulated fluorescent nanocrystal, a functionalized, encapsulated fluorescent nanocrystal labeled with a plurality of nucleic acid molecules, and a combination thereof. As an illustrative example, the nucleic acid molecule may comprise a reactive functionality comprising one or more free amine groups. For example, using methodology described in more detail in Example 3 herein, reactive functionalities of nucleic acid molecules comprising free amino groups, and functionalized, encapsulated fluorescent nanocrystals having surface groups comprising free thiol groups are mixed together in the presence of a component for substitution comprising a cross-linking reagent. The cross-linking reagent has an amino-reactive group at one end, and a thiol-reactive group at the other end. In an alternative embodiment, nucleic acid molecules comprising reactive functionalities comprising free amino-reactive groups (e.g., carboxyl groups) can be coupled to surface groups comprising free amino groups of functionalized, encapsulated fluorescent nanocrystals using methods known in the art. In yet another embodiment, the nucleic acid molecules comprise reactive functionalities comprising free thiol groups which can be coupled to surface groups comprising a reactive functionality of functionalized, encapsulated fluorescent nanocrystals using methods known in the art (e.g., to thiol-reactive groups; or to free amino groups using a cross-linking reagent).

EXAMPLE 5

This example illustrates various embodiments for a method of strand synthesis using functionalized, encapsulated fluorescent nanocrystals which comprise labeled nucleobases according to the present invention. Embodiments, other than those that are described herein for purposes of illustration, for using the functionalized, encapsulated fluorescent nanocrystals according to the present invention in a method of strand synthesis will be apparent to those skilled in the art from the descriptions herein. In one embodiment, provided is a single set comprised of at least four species of functionalized, encapsulated fluorescent nanocrystals which are (a) efficiently excited by a single light source; (b) have closely spaced emission spectra that are spectrally resolvable (distinguishable) by peak emission wavelengths (e.g., allowing simultaneous detection of each individual peak); (c) have emissions of relatively high quantum efficiency; (d) are small enough in size so as to minimize possible steric hinderance as related to incorporation and/or the progression during strand synthesis. For example, in one method of the strand synthesis comprising a modified Sanger-type DNA sequencing protocol, utilized are at least four species of functionalized, encapsulated fluorescent nanocrystals having discrete fluorescence emission spectra (e.g., one species is capable of fluorescing red, one species is capable of fluorescing green, one species is capable of fluorescing yellow, one species is capable of fluorescing orange) and comprising a different chain-terminating nucleobase (e.g., one species comprises ddATP; one species comprises ddTTP, one species comprises ddCTP, one species comprises ddGTP) which may be incorporated into a synthesized strand. The species of labeled chain-terminating nucleobases are used in one or more sequencing reactions, followed by resolving the resultant differentially-labeled synthesized strands (e.g., such as by size, length, or time), exciting the synthesized strands with an excitation light source, and then scanning for detection by a fluorimeter or other suitable detection means that is capable of spectrally resolving the discrete fluorescence spectra of the excited functionalized, encapsulated fluorescent nanocrystals. Hence, the individual chain-terminating nucleobases may be identified, and the sequence of the synthesized strand may be determined.

In another embodiment, the strand synthesis comprises employing functionalized, encapsulated fluorescent nanocrystals are utilized into a sequencing protocol which relies on primer extension followed by base-specific cleavage of primer extension products. In one example of this embodiment, a set of four different species of functionalized, encapsulated fluorescent nanocrystals (e.g., one species is capable of fluorescing red, one species is capable of fluorescing green, one species is capable of fluorescing yellow, one species is capable of fluorescing orange) and comprising a different nucleobase (e.g., one species comprises dATP; one species comprises dTTP, one species comprises dCTP, one species comprises dGTP) are incorporated during strand synthesis, and the synthesized strand is suspended in a moving fluid flow stream; an exonuclease is used to sequentially cleave an individual nucleobase (labeled with a functionalized, encapsulated fluorescent nanocrystal) from the end of the suspended synthesized strand, and each cleaved, labeled nucleobase is maintained in order of cleavage for subsequent detection, spectral resolution, and identification using an appropriate detection system in determining the sequence of a synthesized strand. As will be apparent to one skilled in the art, another variation of this embodiment involves coupling a functionalized, encapsulated fluorescent nanocrystal to the nucleobase after it is cleaved (post-replication, post-cleavage). A preferred detection means may comprise a scanner or reader or other analytical instrument which can detect discrete fluorescence peaks that fall in a spectral range of from about 400 nm to about 900 nm; and, optionally (when more than one color is used in the detection system), distinguish between spectrally resolvable fluorescence peaks within that range.

In another embodiment, the functionalized, encapsulated fluorescent nanocrystals comprising labeled nucleobases are incorporated into a (nucleic acid) strand synthesized in a template-directed manner. A template-directed manner is generally achieved by enzymatic copying template, and insertion of nucleobases in the strand synthesized, by an enzyme that replicates nucleic acids in a template-directed manner using methods known in the art. The strand synthesis may be a process selected from the group consisting of nucleic acid amplification, fill-in reactions, reverse transcription, in vitro mutagenesis, cycled chain termination sequence reactions, cycled primer extension reactions, random primer extension reactions, nick translations, primer elongation, methods for determining the presence and quantifying the number of di- and trinucleotide repeats, and DNA typing with short tandem repeat polymorphisms.

EXAMPLE 6

This example illustrates various embodiments for using functionalized, encapsulated fluorescent nanocrystals which comprise labeled affinity molecules according to the present invention. Embodiments, other than those that are described herein for purposes of illustration, for using the functionalized, encapsulated fluorescent nanocrystals according to the present invention in a method of fluorescence detection will be apparent to those skilled in the art from the descriptions herein. In a method of detection of a target substrate using the functionalized encapsulated fluorescent nanocrystals according to the present invention, the functionalized encapsulated fluorescent nanocrystals are placed in contact with a sample being analyzed for the presence or absence of a substrate ("target substrate) for which the affinity molecule of the functionalized encapsulated fluorescent nanocrystals has binding specificity. Where the affinity molecule portion of the functionalized, encapsulated fluorescent nanocrystals comprises a nucleic acid molecule, the method of detection of a target substrate comprises hybridization (when the target substrate is a nucleic acid molecule) or binding (where the target substrate is a protein). With respect to hybridization, it is known in the art to refer to a process by which a single-stranded nucleic acid molecule joins with a complementary strand through nucleotide base pairing. A sufficient number of complementary base pairs are needed for hybridization, and the selectivity of hybridization depends on the degree of complementarity, the stringency of conditions during the hybridization process, and the length of the hybridizing strands. Thus, in a suitable detection system, a molecular probe comprising functionalized, encapsulated fluorescent nanocrystals is added in a diagnostically-effective amount to a sample being analyzed for the presence or absence of a target substrate in suitable conditions for the molecular probe to contact and bind to target molecule if present in the sample. Typically, a wash step may be performed to remove from the detection system any unbound or nonspecifically bound molecular probe, and then the sample is exposed to an appropriate excitation light source (e.g., depending on the nature of the fluorescent nanocrystals used), and detected (and may include quantitation) is any resultant fluorescence emission spectra. Quantitation of the amount of target substrate present is directly related to the intensity of the emitted fluorescence peak. As known to those skilled in the art of fluorescent nanocrystals, the absorbance peak and fluorescence peak emissions depend on such factors which include, but are not limited to, the chemical nature, the size of semiconductor nanocrystals, and amount of dopant comprising dMO nanocrystals. There are various assay system formats in which such functionalized, encapsulated fluorescent nanocrystals may be used which include, but are not limited to, Northern blot, Southern blot, microarrays (e.g., gene chips, protein chips), in-situ hybridization ("FISH"), screening of nucleic acid molecule libraries, genetic introduction (e.g., transfection, infection, electroporation) efficiency assays, molecular amplification assays (e.g., dendrimer formation as disclosed in co-pending U.S. application Ser. No. 09/437,076; the disclosure of which is herein incorporated by reference), and assays for gene expression.

In a preferred embodiment wherein a functionalized, encapsulated fluorescent nanocrystal comprises one or more nucleic acid molecules, the nucleic acid molecule comprises an expression vector for expression from a desired nucleic acid sequence, or a nucleic acid molecule (e.g., gene), which is desired to be introduced (e.g., infection, transfection, electroporation) into a living cell. For example, the lipid mixture which is used to form the functionalized, encapsulated fluorescent nanocrystals comprises one or more cationic lipids, and one or more "helper lipids" in forming a lipid mixture which confers or facilitates transfection efficiency of the resultant functionalized, encapsulated fluorescent nanocrystals. Helper lipids are known to those skilled in the art to include, but are not limited to, dioleoylphosphatidylethanolamine (DOPE), cholesterol (ch), monooleoylglycerol, dioleoylphosphatidylcholine (DOPC), and a combination thereof. Cationic lipids are known to those skilled in the art to include, but are not limited to, 3(beta) (N-(n',N'-dimethylaminoethane) carbamoyl) cholesterol (DC-ch), N-(1-(2,3-dioleoyloxy) propyl-N,N,N-trimethylammonium chloride (DOTMA), dymyristyloxypropyl-3-dimethyl-hydroxyethyl ammonium (DMRIE), 1,2 dioleoyl-3-trimethylammonium propane chloride (DOTAP), and a combination thereof. It will be apparent to one skilled in the art that the lipid mixture may comprise one or more cationic lipids, or one or more cationic lipids in combination with one or more helper lipids, depending on the desired performance and desired properties. For example, the one or more cationic lipids may comprise from about 10% to about 90% or more of the lipid mixture. Preferred lipid mixtures comprise: DMRIE and DOPE; MMCE and DOPE (1:1); DOTMA and ch (1:1); DOTAP and DC-ch; DMRIE and DC-ch; or DOPE and DC-ch. As apparent to one skilled in the art, the transfection efficiency of a functionalized, encapsulated fluorescent nanocrystal may depend on one or more factors which include, but are not limited to, the structure of the cationic lipids used in its formation, cationic lipid-to-nucleic acid molecule ratio, size of the functionalized, encapsulated fluorescent nanocrystal, and lipid mixture content.

In one embodiment, the functionalized, encapsulated fluorescent nanocrystals are mixed with nucleic acid molecule (including, but not limited to, a plasmid, or other DNA molecule) in suitable ratios and amounts in forming complexes for promoting introduction into the cells desired to be transfected. For example, with respect to cell types and/or transfection conditions in which a negatively charged complex is desired, a relatively higher ratio of nucleic acid to functionalized, encapsulated fluorescent nanocrystals may be utilized. Likewise, for cell types and/or transfection conditions in which a positively charged complex is desired, a relatively higher ratio of functionalized, encapsulated fluorescent nanocrystals to nucleic acid molecule may be utilized. For example, depending on the cell type, the different ratios of nucleic acid molecule: functionalized, encapsulated fluorescent nanocrystals may be used to form the complexes for transfection. Generally, these ratios are expressed in micrograms of nucleic acid molecule:nanomoles of cationic lipid. For purposes of illustration, it is generally known that the ratio may range from about 15:1 to about 1:20 (nucleic acid molecule:cationic lipid). Thus, for example, the nucleic acid molecule and the functionalized, encapsulated fluorescent nanocrystals are added together to form a mixture (e.g., by mixing, and incubating for 15 minutes at room temperature). Alternatively, the nucleic acid molecule may be encapsulated in the functionalized, encapsulated fluorescent nanocrystals by incorporating the nucleic acid molecule (e.g., at the appropriate ratio) during liposome formation, including, but not limited to, in the dried lipid mixture film, or the solution for hydrating the dried lipid mixture film. In either embodiment, the resultant complexes may then utilized in transfection protocols known in the art (e.g., may be added to media and the media is incubated with cells under suitable conditions for transfection, such as 5–6 hours in a tissue culture incubator at 37° C. with $CO_2$). Following this process, the efficiency of introducing the functionalized, encapsulated fluorescent nanocrystals into the cells may be evaluated by subjecting the cells to fluorescence analysis by a method which may include, but is not limited to, fluorescence microscopy, or fluorescence scanner. For example, the cells are exposed to an appropriate excitation light source (e.g., depending on the nature of the fluorescent nanocrystals used), and detected is any resultant fluorescence emission spectra emitted from functionalized, encapsulated fluorescent nanocrystals. Quantitation of the amount of functionalized, encapsulated fluorescent nanocrystals present in the cells is directly related to the intensity of the emitted fluorescence peak.

EXAMPLE 7

This example illustrates various embodiments for a method of using functionalized, encapsulated fluorescent nanocrystals which comprise labeled affinity molecules according to the present invention. Embodiments, other than those that are described herein for purposes of illustration, for using the functionalized, encapsulated fluorescent nanocrystals according to the present invention in a method of fluorescence detection will be apparent to those skilled in the art from the descriptions herein. In a method of detection of a target substrate using the functionalized encapsulated fluorescent nanocrystals according to the present invention, the functionalized encapsulated fluorescent nanocrystals are placed in contact with a sample being analyzed for the presence or absence of a target substrate for which the affinity molecule of the functionalized encapsulated fluorescent nanocrystals has binding specificity. In this embodiment, the affinity molecule portion of the functionalized, encapsulated fluorescent nanocrystals comprises a protein with binding specificity (e.g., monoclonal antibody, peptide, lectin) or an aptamer with binding specificity. The functionalized, encapsulated fluorescent nanocrystals are contacted with the sample being analyzed for the presence or absence of a target substrate. Subsequent binding, between the affinity molecule portion of the functionalized, encapsulated fluorescent nanocrystals and the target substrate, if present in the sample, in a detection system results in complexes comprising the functionalized, encapsulated fluorescent nanocrystal-target substrate which can emit a detectable signal for quantitation, visualization, or other form of detection. Upon formation of the complexes comprising the functionalized, encapsulated fluorescent nanocrystal-substrate, the detectable signal emitted therefrom may be detected by first exposing the complexes formed in the detection system to an excitation spectra of light (UV or other suitable light source; depending on the nature of the fluorescent nanocrystal used) that is suitable for exciting the functionalized, encapsulated fluorescent nanocrystals to emit a fluorescence peak. The peak is then detected, or detected and quantitated, by appropriate detection means (e.g., photodetector, filters, fluorescence microscope, and the like). Quantitation of the amount of target substrate present is directly related to the intensity of the emitted fluorescence peak. As known to those skilled in the art of fluorescent nanocrystals, the absorbance peak and fluorescence peak emissions depend on such factors which include, but are not limited to, the chemical nature, and amount, of the dopant comprising dMO nanocrystals; and the chemical nature and size of semiconductor nanocrystals. As will be apparent to one skilled in the art, the detection system may include, but is not limited to, a fluorescence-based immuno-assay, fluorescence-based detection systems, fluorescent staining (e.g., immunofluorescent staining on a glass slide), microarrays, flow cytometry, molecular tracking (e.g., locating or tracking a target substrate), molecular sorting (e.g., cell sorting by flow cytometry), fluorescence imaging (e.g., of live tissue, or fiber optic fluorescence imaging microscopy), and the like.

EXAMPLE 8

In another illustration of a method for using functionalized, encapsulated fluorescent nanocrystals, it may be desirable to quench (reduce or eliminate) the fluorescence signal emitted by functionalized, encapsulated fluorescent nanocrystals present in a detection system (particularly a detection system which may use an aqueous solution; e.g., an immunoassay, microarray, and the like). To illustrate this example, and wherein the functionalized, fluorescent nanocrystals are present in an aqueous-based solution (either before or after treatment with the lipolytic agent), the liposome portion of the functionalized, encapsulated fluorescent nanocrystals may be disrupted to release the fluorescent nanocrystals. The fluorescent nanocrystals, being insoluble in aqueous solutions, can form aggregates when they interact together which can cause irreversible flocculation of the fluorescent nanocrystals. Thus, a method of quenching fluorescence, in a detection system, from a substrate comprising functionalized, encapsulated fluorescent nanocrystals comprises: contacting the functionalized, encapsulated fluorescent nanocrystals with a lipolytic agent in an effective amount to disrupt liposome portions of the functionalized, encapsulated fluorescent nanocrystals in releasing fluorescent nanocrystals; and removing the released fluorescent nanocrystals from the detection system (e.g., by allowing the released fluorescent nanocrystals to precipitate in an aqueous-based solution thereby removing it from the substrate, and/or washing the released fluorescent nanocrystals from the detection system) in quenching the fluorescence.

Also, when the liposome portion of the functionalized, encapsulated fluorescent nanocrystals is disrupted, the released fluorescent nanocrystals may be washed from the system (using a solution appropriate for the detection system, as is standard in the art). For example, where the affinity molecule portion of the functionalized, encapsulated fluorescent nanocrystals is bound to a target substrate in the system, thereby immobilizing the functionalized, encapsulated fluorescent nanocrystals, disruption of the liposome portion will release the fluorescent nanocrystals from being immobilized. As apparent to one skilled in the art, there are several means by which the liposome portion of functionalized, encapsulated fluorescent nanocrystals may be disrupted. For example, a lipolytic agent for disrupting the liposome portion includes, but is not limited to, a lipolytic enzyme, components of the complement system sufficient to cause complement-mediated lysis, a detergent (e.g., a non-ionic detergent such as TRITON X-100; saponin; and the like), a water-miscible alcohol, and a combination thereof. Briefly, the functionalized, encapsulated fluorescent nanocrystals are contacted with an amount of the lipolytic agent effective to cause disruption (breakage or lysis) of the functionalized, encapsulated fluorescent nanocrystals. Depending on the lipolytic agent, and the time in which to achieve the desired disruption, an amount of a lipolytic agent effective to cause such lysis or disruption may comprise from about 10% to about 90% of the volume of the aqueous-based solution comprising the functionalized, encapsulated fluorescent nanocrystals to be disrupted. The released fluorescent nanocrystals may then be removed or excluded from the detection assay or system.

EXAMPLE 9

As previously described herein in more detail, a method of making functionalized, encapsulated fluorescent nanocrystals according to the present invention comprises the steps of: (a) mixing fluorescent nanocrystals with a lipid mixture comprising the lipids (e.g., one or more phospholipids, or one or more phospholipids and one or more sterols) to form a dried lipid mixture film; (b) contacting the dried lipid mixture film with an aqueous solution; and (c) mixing the dried lipid mixture film with the aqueous solution in forming functionalized, encapsulated fluorescent nanocrystals. The mixing step (c) may be performed by any method known in the art which includes, but is not limited to, vortexing, sonication, applying pressure, extrusion, injection, and a combination thereof. As apparent from the descriptions herein, the dried lipid mixture film comprises the lipids desired to form the liposome portion of the functionalized, encapsulated fluorescent nanocrystals; and in an alternative embodiment, the lipid mixture may further comprise one or more components for substitution. As apparent from the descriptions herein, the aqueous solution may further comprise one or more components for substitution, affinity molecule, or a combination thereof. The method according to the present invention may further comprise post-treating the functionalized, encapsulated fluorescent nanocrystals by contacting the functionalized, encapsulated fluorescent nanocrystals with one or more components for substitution under suitable conditions for the one or more components for substitution to become part of the liposome portion of the functionalized, encapsulated fluorescent nanocrystals. As apparent from the descriptions herein, the one or more components for substitution comprises one or more affinity molecules which have a reactive functionality that is coupled to the reactive functionality of the liposome portion of the functionalized, encapsulated fluorescent nanocrystals. Additionally, the method may further comprise a purification step (e.g., size exclusion, density separation, separation based on solubility, magnetic separation based on magnetic attraction of the encapuslated fluorescent nanocrystals to a magnet source, and the like) to purify the desired population of functionalized, encapsulated fluorescent nanocrystals. As previously described herein in more detail, one embodiment of mixing fluorescent nanocrystals with a lipid mixture to form a dried lipid mixture film comprises mixing the fluorescent nanocrystals and lipid mixture in the same organic solvent, and then evaporating the solvent to form the dried lipid mixture film.

Alternatively, the fluorescent nanocrystals in a solvent may be evaporated to form a dried preparation of fluorescent nanocrystals, the lipid mixture may be dried, and then the dried preparation of fluorescent nanocrystals and dried preparation of lipid mixture may be mixed together to form the dried lipid mixture film.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A functionalized, encapsulated fluorescent nanocrystal comprising:
    a liposome;
    one or more fluorescent nanocrystals encapsulated by the liposome; and surface groups, wherein an outer surface of the liposome comprises the surface groups, and wherein the surface groups are selected from the group consisting of one or more reactive functionalities, one or more affinity molecules, and a combination thereof.

2. The functionalized, encapsulated fluorescent nanocrystal according to claim 1, wherein the surface groups comprise an affinity molecule comprising a monoclonal antibody.

3. The functionalized, encapsulated fluorescent nanocrystal according to claim 1, wherein the surface groups comprise a reactive functionality coupled to an affinity molecule comprising a monoclonal antibody.

4. The functionalized, encapsulated fluorescent nanocrystal according to claim 1, wherein the surface groups comprise an affinity molecule comprising a nucleobase.

5. The functionalized, encapsulated fluorescent nanocrystal according to claim 1, wherein the surface groups comprise a reactive functionality coupled to an affinity molecule comprising a nucleobase.

6. The functionalized, encapsulated fluorescent nanocrystal according to claim 1, wherein the surface groups comprise an affinity molecule comprising a nucleic acid molecule.

7. The functionalized, encapsulated fluorescent nanocrystal according to claim 1, wherein the surface groups comprise a reactive functionality coupled to an affinity molecule comprising a nucleic acid molecule.

8. The functionalized, encapsulated fluorescent nanocrystal according to claim 1, wherein the liposome is comprised of one or more cationic lipids and one or more helper lipids in forming a liposome adapted for transfection.

* * * * *